United States Patent
Coope et al.

(10) Patent No.: US 6,302,119 B1
(45) Date of Patent: Oct. 16, 2001

(54) LOW ODOR PERMANENT WAVING COMPOSITIONS CONTAINING A DISULFIDE

(75) Inventors: Janet Lynn Coope, Norwalk; Renee E. Nardone, Trumbull, both of CT (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/455,232

(22) Filed: Dec. 6, 1999

(51) Int. Cl.$^7$ ................................................. A45D 24/06
(52) U.S. Cl. ................................................................ 132/204
(58) Field of Search ..................................... 132/200, 202, 132/203, 204, 205, 206; 424/62, 70.1, 70.2, 70.4, 70.5, 70.51

(56) References Cited

U.S. PATENT DOCUMENTS

| | | |
|---|---|---|
| 3,693,633 * | 9/1972 | Kalopissis et al. ............... 132/202 |
| 3,768,490 | 10/1973 | Kalopissis et al. . |
| 3,892,845 * | 7/1975 | Cunningham et al. ............. 424/62 |
| 3,951,156 * | 4/1976 | Gadzala et al. .................. 132/202 |
| 4,547,365 | 10/1985 | Kubo et al. . |
| 4,560,554 | 12/1985 | Kubo et al. . |
| 4,812,307 | 3/1989 | Siuta-Mangano . |
| 4,851,215 | 7/1989 | Smith et al. . |
| 5,085,858 | 2/1992 | Halloran et al. . |
| 5,184,630 | 2/1993 | Jung . |
| 5,540,910 | 7/1996 | Samain et al. . |
| 5,554,363 | 9/1996 | Nandagiri et al. . |
| 5,554,364 | 9/1996 | Neill et al. . |
| 5,715,845 | 2/1998 | Samain . |
| 5,776,454 | 7/1998 | Gee et al. . |
| 5,843,420 | 12/1998 | Bauer et al. . |

FOREIGN PATENT DOCUMENTS

| | | |
|---|---|---|
| 0 246 090 A2 | 11/1987 | (EP) . |
| 0 302 265 A1 | 2/1989 | (EP) . |
| 0 459 500 A2 | 12/1991 | (EP) . |
| 10-101534 | 4/1998 | (JP) . |
| 90-00385 | 1/1990 | (WO) . |
| 93/06817 | 4/1998 | (WO) . |

OTHER PUBLICATIONS

Borish, Hair and Hair Care, 1997, pp. 167–190.

* cited by examiner

Primary Examiner—John J. Wilson
Assistant Examiner—Eduardo C. Robert
(74) Attorney, Agent, or Firm—Charles J. Zeller

(57) ABSTRACT

This invention provides compositions and methods for reducing odors associated with permanent hair waving by contacting the hair with a disulfide before, during, or after application of a sulfur-based reducing agent.

34 Claims, No Drawings

LOW ODOR PERMANENT WAVING COMPOSITIONS CONTAINING A DISULFIDE

FIELD OF THE INVENTION

The present invention relates to compositions and methods for reducing odors associated with agents used in permanent hair waving processes. Specifically, the present invention relates to disulfides that lower odor during hair processing and that lower post-perm odor.

BACKGROUND OF THE INVENTION

In general, permanent waving of hair is effected by chemically cleaving the disulfide bonds that occur naturally in hair with a reducing agent, optionally rinsing, and forming new disulfide bonds with an oxidizing agent while the hair is under tension. Permanent waving can be used to either increase or decrease the amount of curl in hair.

Sulfur containing agents are commonly used to reduce the disulfide bonds in hair. These agents include organic thiol containing compounds and inorganic sulfur containing compounds and are used either individually or in combination. Examples of organic thiols used in waving compositions are compounds such as cysteine, cysteamine, N-substituted cysteamines, alkyl substituted mercaptoacetamides, dimercaptoadipic acid, thioglycerol, thiolactic acid, thioglycolic acid or its salts, (e.g., a thioglycolate), monothioglycolic acid esters such as diol esters of thioglycolic acid, glyceryl monothioglycolate, thiocholine or its salts, amino thiols, and thiols attached to low molecular weight polymers. Examples of inorganic reducing agents used in waving compositions are compounds such as sodium hyposulfite and ammonium or sodium bisulfite.

One of the most obvious and negative characteristics of a permanent wave is the strong chemical odor. For example, in many commercially available wave kits an unpleasant odor is produced by the thiol reducing agent as well as from ammonia. In addition to the odor produced during the treatment process, hair is often left with a "sulfur" smell that can take days or weeks to dissipate. The cause of the odor may be due to the sulfur containing reducing agent itself or a degradation product.

Many permanent waves are based on thioglycolic acid (TGA). This reagent shows good performance, low cost, low damage and good toxicology. The major disadvantages of TGA is the unpleasant odor and high pH at which is must be used, which is considered damaging. Thiolactic acid is less efficient than TGA but is milder on the epidermis. It is sometimes used in combination with TGA. Glyceryl monothioglycolate (GMT) has been used for a number of years in "acid waves", which are formulated at a pH of about 7–8. A low pH formulation is possible because of the lower pKa of this thiol (7.8) compared to thioglycolic acid (10.4). These waves are considered softer and less damaging than those obtained from TGA, presumably due to the lower pH. The disadvantage of this reagent is that it causes skin irritation in some people. In addition, the post-perm odor is more pronounced from GMT (glyceryl monothioglycolate) acid waves, than from ATG (ammonium thioglycolate) alkaline waves.

Cysteamine has a pKa of 8.6, so it may be formulated at a pH near 8. The major disadvantage of this reagent is the post-penn odor which has a different characteristic than thioglycolic acid. This odor has been likened to burnt popcorn or corn chips. Another agent, cysteine, which has been marketed in Japan as a natural reagent, produces weaker curls than TGA and is an irritant. Another problem with cysteine is that its corresponding disulfide by-product forms a water-insoluble precipitate which looks like flakes of dandruff. It has a high pKa (10.8) and thus, as with TGA, ester derivatives are used to lower the pKa of the thiol and allow for lower pH formulations.

Thiols, also known as mercaptans, are known to degrade to hydrogen sulfide via both radical and nucleophilic mechanisms. In fact, gas chromatography has been used to detect ppm levels of hydrogen sulfide in the headspace of ammonium thioglycolate waving compositions' and of methyl mercaptan in the headspace of a vessel containing hair permed with ammonium thioglycolate.[2] Post-penn odor is also attributed to the disulfide byproduct that is formed from the reaction of K—S—S—K+2 R—S—H→R—S—S—R+2 K—S—H, where K= hair keratin.[3] This explanation would account for the greater post-penn odor from GMT since this disulfide will be less water soluble than the disulfide from ATG and, thus, less effectively washed away. Other evidence suggests that the thiols become physically or chemically bound to the hair during the penning process.[4]

The odor released by the sulfur-based waving compositions is a significant drawback and many unsuccessful attempts have been made to mask the odor with perfumes. In addition, attempts have been made to remove the malodorous compounds. For example, U.S. Pat. No. 5,184,630 describes an aqueous suspension of siliceous crystalline molecular sieves to remove post-perm odor on hair. U.S. Pat. No. 4,560,554 describes the incorporation of between 0.0001 and 5 weight percent of a ketone, such as dibenzyl ketone or 2-hydroxyl-1,4-napthoquinone, to the hydrogen peroxide neutralizer to eliminate mercaptan odor on hair. U.S. Pat. No. 4,547,365 describes the incorporation of a ketone and a cyclodextrin in the mercapto waving composition to lower odor. U.S. Pat. No. 5,843,420 describes the addition of a powdered, odor removing absorbing agent which is insoluble in the thiol containing waving composition formulation. EP 246,090 describes the reduction of perm odor by using a cyclodextrin in conjunction with a cationic polymeric material together in a thioglycolate waving composition or contained in a post-perm shampoo. U.S. Pat. No. 5,715,845 describes the use of a manganese salt prior to, or during, the reduction step to lower the post-perm odor. WO 90/00385 describes the use of between 0.05 and 5 weight percent of peroxydisulfate with a hydrogen peroxide neutralizer to eliminate post-penn odor from hair due to higher oxidizing ability of persulfate. EP 302,265 describes the incorporation of isosorbide dimethyl ether into a thiol containing wave composition. JP 10 101,534 describes an antibacterial substance derived from dry distillation of higher plants to remove malodor.

In addition, work has focused on improving cysteamine post-perm odor. Researchers have found that odor can result from reaction between hair aldehydes and cysteamine and have employed chemicals to competitively react with either of these components. One theory is that post-perm odor results from odoriferous residues made up of thiazolidine compounds that are formed upon reaction of the aldehydes in the hair with the thiol reducing agent.[5] These residues remain in the hair, either because they are chemically bound or trapped within the hair matrix. Over time the residues are released and the odor is noted.[6] Use of polyhydric phenols, such as resorcinol or its derivatives, reduce the post-perm odor because they react with hair aldehydes thus blocking these sights from the reducing agent (U.S. Pat. No. 5,554, 364). These polyhydric phenols may be used before, during or after treatment with reducing solution, or after neutralization since they are said to be substantive to hair; they are particularly useful when cysteamine is the reducing agent A related approach involves treating hair with an aldehyde solution either before treatment with cysteamine or after, but before neutralization (U.S. Pat. No. 5,554,363 and 5,554,363). These aldehydes compete with the hair aldehydes for the residual reducing agent and produce a different, more pleasant odor. Benzaldehyde or methyl hydrocinnamic aldehyde is preferred since they react faster than hair aldehydes. Presumably the reaction of thiols with aldehydes is slower than their reaction with hair disulfides. A similar patent, U.S. Pat. No. 5,540,910, describes a process in which specific aliphatic aldehydes are applied to hair after the reduction step, and either before or after neutralization (U.S. Pat. No. 5,540,910). The use of thioglycolic acid after cysteamine is reported to prevent odor (WO 9306817)

However, none of these methods eliminate or reduce the perm-associated malodor to acceptable levels. According to the present invention, disulfides are used to reduce perm-associated malodor during permanent waving, and/or to reduce malodor on hair after permanent waving. Although the use of disulfides with thiol reducing agents is described in the prior art as a method for providing "stop-action" or "self-timing" waves, these disulfides are used at concentrations much higher relative to thiol than in the present invention. The ratio of disulfide to thiol is typically 1:20 to 1:5 in these "stop action" products. A self-neutralizing wave at even higher disulfide to thiol ratio is described in U.S. Pat. No. 3,768,490. The use of disulfides as a neutralizer and as an additive to hair waving compositions has also been described. For example, the use of glutathione disulfide to crosslink hair thiols is described in U.S. Pat. No. 4,812,307, and the use of pantethine to improve waving efficiency in permanent waving is described in U.S. Pat. No. 4,851,215. However, none of the prior art patents describe the odor reducing properties of disulfides which are taught in the present invention.

SUMMARY OF INVENTION

The present invention provides compositions useful for reducing odor related to sulfur-based reducing agents used to permanently wave hair. The present invention also provides permanent hair waving compositions with reduced odor. In one aspect of the invention, a pretreatment composition is provided which comprises a disulfide. In another aspect of the invention a sulfur-based activator composition comprising a disulfide is provided. The activator composition can be either part of an acid wave or an alkaline wave. In yet another aspect of the invention a neutralizer composition comprising a disulfide is provided. In yet another aspect of the present invention, a post-treatment composition, such as a shampoo, is provided which comprises a disulfide. More than one disulfide may be formulated with any one of the compositions according to this invention.

In an embodiment of the invention, a wave system comprising at least one disulfide is provided as a kit The kit may contain one or more of the following compositions contained in a suitable container: a pretreatment or wrapping composition, a sulfur-based activator composition with or without a balancing solution, a neutralizing composition, and a post-treatment composition or shampoo, wherein at least one of the compositions comprises a disulfide. Alternatively, the kit may contain one or more of a pretreatment or wrapping composition, a sulfur-based activator composition with or without a balancing solution, a neutralizing composition, and a post-treatment composition or shampoo, and the disulfide is provided in a separate and suitable container to be added to one or more of the compositions prior to or during the waving process.

The present invention also provides a method of reducing malodor resulting from contact of hair with a sulfur-based reducing agent to cleave the hair disulfide bonds and subsequent contact of the hair with an oxidizing agent to form new hair disulfide bonds. The method comprises contacting the hair with a disulfide prior to, during, or after contacting the hair with a sulfur-based reducing agent.

In another embodiment of the invention, a process for the permanent deformation of hair wherein the process has reduced odor is provided. The hair is optionally contacted with a pretreatment or wrapping solution. A sulfur-based activating composition is then contacted with the hair which has previously been put under tension. The waving composition is optionally rinsed from the hair and a neutralizing composition is applied to the hair. An optional post-treatment is then provided. Odor is reduced in the above process by contacting the hair, before, during, and/or after application of the sulfur-based activating composition with a disulfide.

DETAILED DESCRIPTION OF THE INVENTION

In accordance with the present invention, reduction of the malodor incident to a permanent waving procedure is achieved by contacting the hair before, during or after the permanent waving procedure, with a composition comprising a disulfide. A variety of disulfides are useful according to the present invention to reduce the odor resulting from treatment of hair with a sulfur-based reducing agent. Non-limiting examples of such disulfides include, for example, dithiodiglycolamide siloxanes, silicone disulfides, water-soluble disulfides and water-insoluble disulfides.

In one embodiment, dithiodiglycolamide siloxanes are formulated with the compositions or used according to the methods of the present invention. Dithiodiglycolamide siloxanes are prepared from the corresponding thioglycolamide-functional functional siloxanes by the dimethyl sulfoxide oxidation described in Example 1. The preparation of thioglycolamide-functional siloxanes is known in the art and described in, for example, U.S. Pat. No. 5,085,858. The entire disclosure of U.S. Pat. No. 5,085,858 is incorporated herein in its entirety by reference thereto. Briefly, thioglycolamide-functional siloxanes are prepared from the reaction between an amine-functional siloxane or polysiloxane and thioglycolic acid or thioglycolic acid derivatives, forming a salt, with subsequent dehydration to form the thioglycolamide functional siloxane. Thioglycolamide-functional siloxanes can also be prepared by the reaction between the amine functional polysiloxanes and a thioglycolic ester or a derivative of a thioglycolic ester. The thioglycolamide-functional siloxanes can be prepared from amine-functional siloxanes that are commercially available or prepared by known methods. The amine-functional siloxanes useful in this invention may be polymers or copolymers that are linear or cyclic in structure. It is preferred that primary amine-functional siloxanes be used, however, secondary amine-functional siloxanes can also be used.

In another embodiment, silicone disulfides are formulated with the compositions or used according to the methods of the present invention. Silicone disulfides are prepared from the corresponding mercaptosilicones by the dimethyl sulfoxide oxidation described in Example 1. The preparation of mercaptosilicones is known in the art and described in, for example, U.S. Pat. No. 5,776,454. The entire disclosure of U.S. Pat. No. 5,776,454 is incorporated herein in its entirety by reference thereto. Briefly, mercaptosilicones are prepared, most preferably, by emulsion polymerization techniques described in European Patent Application 0 459 500, published Dec. 4, 1991. To prepare the emulsion, mercaptoalkyl alkoxysilanes are copolymerized with a cyclic polysiloxane in emulsion polymerization, to form white opaque emulsions, translucent, or clear microemulsions. These emulsions and microemulsions may be cationic or anionic. Emulsions produced by this emulsion polymerization technique typically contain silicone concentrations of 10–70 percent by weight of the total emulsion solution. The preferred level of silicone is 25–60 percent by weight. The larger the particle size, the higher the concentration of silicone the emulsion may contain. Emulsions may be produced containing less than 10 percent by weight of silicone. While mercapto-functional silicones can be made by emulsion polymerization techniques other than those specifically described in EP 459500, preparation of these emulsion polymers by the emulsion polymerization process in EP 459500 is preferred, due to its economic advantage and high degree of particle size control.

In another embodiment, the disulfide for use with the compositions or methods of the present invention is a water-insoluble disulfide. The solubility of the disulfide according to this embodiment preferably is such that the disulfide have a log P value greater than about 1. More preferably, the disulfide of this embodiment has a log P value of about 3 or greater, and most preferably, about 5 and above.[7] Table 1 provides non-limiting examples of disulfides for use according to this embodiment. The log P values were calculated using CaChe software from Oxford Molecular Group, Inc. Additional non-limiting examples of disulfides for use according to this embodiment are disulfides such as dithiodicitronollol which is more pleasant smelling, dithiodilinalol, dithioditerpineol, 3-[1,2-(hydroxyethyl) butyldisulfanyl]-hexan-1-ol, and more reactive cyclic disulfides such as 6,8-dithiooctanoic acid or its alkyl esters.

Table 2 describes several water-soluble disulfides. In general, water-soluble disulfides will partition into the water phase and may react with the active thiol reducing agent giving a mixed disulfide that is less effective at removing odors. In general, these water-soluble disulfides are less effective at removing odors. As used herein, "water-insoluble" means the solubility of the disulfide in water relative to octanol and wherein the disulfide has a log P of at least 1. In fact, the addition of dithiodiglycolic acid (DTG) to an activator composition did not diminish the processing or post perm odor. However, acceptable results have been obtained with pantethine. Pantethine is preferably formulated such that it comprises between less than about 0.005% and 0.00001% of the total composition. More preferably, pantethine is formulated so that it comprises between less than about 0.01% and about 0.00001% of the composition based on the amount of sulfur-based activator and most preferably between less tan about 0.005% and about 0.00001% based on the amount of the sulfur-based activator. Acceptable results have also been obtained using glutathione disulfide which is formulated in similar amounts to pantethine.

TABLE 1

| | log P |
|---|---|
| dithiodigeraniol | 6.52 |
| n-dodecyl 1,2-dithiolane-3-pentanoate | 6.19 |
| di-n-heptyl disulfide | 5.86 |
| di-n-octyldithiodiglycolate | 5.80 |
| di-i-octyldithiodiglycolate | 5.67 |
| n-decyl-1,2-dithiolane-3-pentanoate | 5.40 |
| n-octyl-1,2-dithiolane-3-pentanoate | 4.61 |
| i-octyl-1,2-dithiolane-3-pentanoate | 3.89 |
| n-butyl-1,2-dithiolane-3-pentanoate | 3.02 |
| di-n-butyldithiodiglycolate | 2.63 |
| 5-phenyl-1,2-dithio-3-one | 2.04 |

TABLE 2

| | log P |
|---|---|
| dithiodiglycolic acid (DTG) | −0.50 |
| N,N'-diacetylcysteamine | −0.86 |
| diglyceryldithiodiglycolate | −1.42 |
| pantethine | −1.94 |
| glutathione disulfide | −5.00 |

The disulfide of this invention can be formulated with the sulfur-based reducing agent. There are two types of waving lotions commonly used to permanently wave hair—an acid wave and an alkaline wave. The acid wave is typically formulated as a two component activator composition. One component is the reducing agent, typically GMT, and the second component is a balancing solution. These are often packaged separately. The disulfide can be formulated with either the reducing solution or the balancing solution. The alkaline wave is typically formulated as a single composition into which a disulfide can be formulated. Preferably, the disulfide is compatible in the solution in which it is formulated. Alternatively, the disulfide can be provided in a separate container and added to the reducing agent prior to or during use in both the acid wave or alkaline wave compositions.

The disulfide of this invention may be used with any sulfur-based reducing agent known to reduce hair disulfide bonds. The wave compositions or lotions typically comprise a sulfur-based reducing agent such as an organic thiol and/or an inorganic sulfur-containing compound in an aqueous based solution. For an acid wave, the reducing agent (activator), typically GMT, is usually provided separate from a balancing solution (acid wave base). The reducing agent and balancing solution are then mixed prior to application. For an alkaline wave, the reducing agent is usually formulated in a basic aqueous solution. The base is often ammonia. Some examples of sulfur-based reducing agents useful in the present invention include, but are not limited to, compounds such as cysteine, cysteamine, N-acetylcysteamine, thioglycerol, thiolactic acid, thioglycolic acid or its salts, (e.g., ammonium thioglycolate), monothioglycolic acid esters such as glyceryl monothioglycolate, thiocholine or its salts, sodium hyposulfite and ammonium or sodium bisulfite. More preferred reducing agents for use according to this invention are organic thiols. More preferred examples of reducing agents are ammonium thioglycolate, esters of thioglycolic acid, and glyceryl monothioglycolate, ammonium thiolacetate, cysteine, and cysteamine. A particularly preferred reducing agent is glyceryl monothioglycolate (GMT). Although there is no specific limitation to the amount of reducing agent contained in the wave composition, the reducing agents are preferably incorporated into the waving composition in the amount of between about 1% to about 18% by weight, more preferably between about 5% to 15%, and most preferably between about 7% to about 11% by weight, based on the total weight of the waving composition.

The disulfide can be incorporated into a pretreatment composition, an activator or activator balancing solution, a neutralizer composition, a post-treatment composition, or in a combination thereof. The disulfide is preferably incorporated into the neutralizer composition or the activator or activator balancing solution. Alternatively, the disulfide is provided in a separate container and added to one or more of the above compositions prior to or during the permanent waving procedure. The compositions containing the disulfide compound can contain various additional cosmetic ingredients such as, for example, an anionic, nonionic, amphoteric, zwitterionic or cationic surfactant, an alkalinizing or acidifing agent, a preservative, a stabilizer, a treating agent such as cations and polymers, a dye, a sunscreen agent, a thickening agent, buffers and lustering agents. The pH of the compositions of the invention should be in the range of about 1.5 to about 11. A pH outside of this range can cause irritation to the skin and scalp and/or result in instability of the composition. A preferred pH range is from about 3 to about 10.5. A preferred pH range for the activator is from about 2 to about 4. A preferred pH range for the activator balancing solution is from about 9 to about 11. A preferred pH range for the waving lotion, which is a mixture of the activator and activator balancing solution, is from about 7 to about 9.

Suitable non-limiting examples of pretreatment compositions are based on aqueous and aqueous/alcoholic systems containing a disulfide, and further containing one or more of the following in a compatible combination: a low molecular weight alcohol or polyol, a low molecular weight carboxylic acid, e.g., citric acid, a lipoidol alkyl chain having ten or more carbons, a polysiloxane such as methylpolysiloxane, a paraffin compound, a cationic conditioning agent, a capillary active and an ampholytic imidazole conditioning agent.

The concentration of the disulfide in the pretreatment compositions varies according to whether or not the pretreatment composition is washed out of the hair prior to applying the waving composition. In any event, the amount of disulfide that remains on the hair should be between about 0.00005 and about 5 weight percent based on the active reducing agent contained in the waving composition to be used. A more preferred amount of disulfide that remains on the hair prior to application of the activator is between about 0.0005 and about 0.5 weight percent and a more preferred range is between about 0.001 and about 0.05 weight percent based on the active reducing agent contained in the waving composition to be used. The most preferred pretreatment composition leaves in about 0.001 to about 0.05. Alternatively, a pretreatment composition comprising about 0.05% to about 2% or, more preferably, about 0.005% to about 0.25% disulfide is provided. The use of this pretreatment composition will leave a satisfactory amount of disulfide in the hair upon washout.

The concentration of the disulfide when formulated with the sulfur-based reducing agent should be between about 0.00005 and about 5 weight percent based on the active reducing agent contained in the waving composition. A more preferred amount of disulfide is between about 0.0005 and about 0.5 weight percent and a more preferred range is between about 0.001 and about 0.05 weight percent based on the active reducing agent contained in the waving composition.

The disulfide of this invention can be incorporated into a neutralizer composition. Neutralizing compositions can contain as the oxidizing agent a peroxide such as hydrogen peroxide, an alkaline bromate, a persalt, a polythionate or mixtures thereof. Although there is no specific limitation to the amount of oxidizing agent contained in the neutralizing composition, the oxidizing agents are preferably. incorporated into the neutralizing composition in the amount of between about 0.5% to about 25% by weight, more preferably between about 1% to 20%, and most preferably between about 1% to about 10% by weight, based on the total weight of the neutralizing composition.

The disulfide of this invention can be applied to the hair after applying the waving lotion as a post-treatment composition. For example, the disulfide of this invention can be formulated with the neutralizer or as a separate post-treatment composition. The post-treatment composition can be applied concurrent with the neutralizer, after application of the neutralizer or after washing out the neutralizer. Preferably, these compositions are aqueous based solutions which may contain one or more of the following constituents in a compatible combination: a glycolic acid, maleic acid, 1,4-cyclohexenone compounds, an essential oil which contains an ethylene bond, 0.1–10 weight percent of an organic acid or its salts such as zinc salts, germanium, antimony, bismuth, and extracts of orange or peppermint.

The concentration of the disulfide in the post-treatment and/or neutralizing composition should be between about 0.00005 and about 5 weight percent based on the active reducing agent contained in the waving composition used or that remains on the hair after rinsing away the activator. A more preferred amount of disulfide is between about 0.0005 and about 0.5 weight percent and a more preferred range is between about 0.001 and about 0.05 weight percent based on the active reducing agent contained in the waving composition used or that remains on the hair after rinsing away the activator. The most preferred amount of disulfide is between about 0.005 and about 0.25 weight percent. The most preferred amount of disulfide incorporated into the neutralizing composition is between about 0.002% to about 0.01% by weight.

The disulfide of this invention can be used with other odor reducing methods and compositions. In addition, other additives can be included in the compositions according to this invention. For example, anti-oxidants, e.g. erythorbic or ascorbic acid, which prevent generation of hydrogen sulfide, zinc salts of an organic acid, terpenes such as citral or limonene, dimethyl isosorbitol, manganese salts, and perfume oil mixed into the composition before use.

The term "composition" is intended to include pretreatment or wrapping compositions, sulfur-based reducing compositions, balancing compositions neutralizing compositions, and post-treatment compositions. These compositions can be formulated as aqueous solutions, gels, emulsions, foams, shampoos and the like.

The disulfide has to be compatible in the system in which it is contained. Thus when formulating the disulfide directly with the sulfur-based reducing agent, it is preferred that the disulfide be substantially insoluble in the wave composition to prevent reaction with the active sulfur-based reducing agent. This is particularly important when formulating an alkaline wave composition or when formulating the disulfide directly in the acidic reducing agent. For example, if the disulfide is incorporated in a GMT-containing composition, the disulfide should be present in a manner that does not allow reaction with the GMT. This can be achieved if the disulfide is not soluble in the GMT and not soluble in the combined GMT-water solution. To avoid possible reaction with the reducing agent, the disulfide can be formulated with the balancing solution. If contained in an alkaline ammonia-containing wave lotion, the disulfide should also be resistant to attack from ammonium hydroxide. Water-insolubility is a way to achieve this stability when the disulfide may be alkaline labile.

A possible mechanism of odor removal for the disulfide may be due to reaction of the disulfide with volatile thiols such as hydrogen sulfide or methyl sulfide to form a mixed disulfide that is less odorous (Scheme 1). For example, the disulfide di-i-octyldithiodiglycolate, either in solution or in the vapor phase, can react with volatile malodorous thiols. The resulting products, which in this case, are more water soluble than the disulfide, are then washed away.

the solvent in vacuo provided 8.43 g (83%) of the title compound as a faintly yellow liquid. $^1$H NMR (CDCl$_3$) δ4.18–4.05 (2H, m, CH$_2$O), 3.49 (2H, s, C(O)CH$_2$S), 1.70–0.75 (15H, m); direct probe mass spec=406 (M).

Preparation of Dithiodieeraniol

Thiogeraniol (supplied by Penta International) is treated with dimethylsulfoxide and worked-up according to the procedure described for di-i-octyldithiodiglycolate.

Preparation of 8,8'-Dithiomenthone

8-Mercaptomenthone (supplied by Aldrich Chemical) is treated with dimethylsulfoxide and worked-up according to the procedure described for di-i-octyldithiodiglycolate.

Preparation of n-Decyl-1,2-dithiolane-3-oentanoate 1,2-Dithiolane-3-pentanoic acid (10.0 g, 0.048 mol, supplied by Aldrich Chemical) is combined with 4,4-(dimethylamino)pyridine (6.51 g, 0.0533 mol), 1-(3-dimethylaminopropyl)-3-ethylcarbodiimide hydrochloride Scheme 1.
Proposed reaction pathway for removal of odorous hydrogen sulfide.

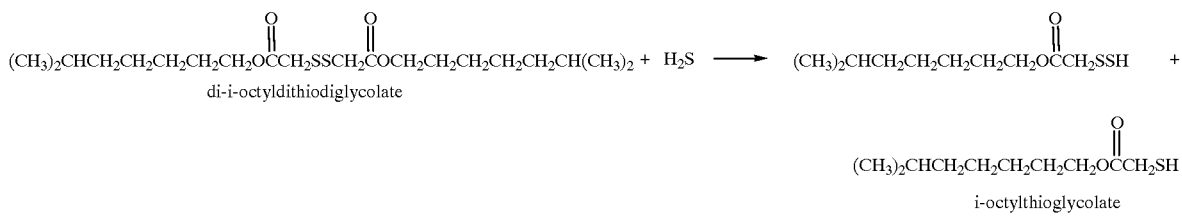

The odor of the disulfide itself should be considered when selecting a disulfide for use according to this invention. For example, the volatility of the disulfide should be such that it does not evaporate too readily. If the disulfide evaporates too readily it may contribute to the overall malodor of the wave composition. This may be the reason why dibutyldithioglycolate has less of an odor reducing effect compared to di-i-octyldithiodiglycolate. By simply varying the volatility of a disulfide in a formulation containing a reducing agent of interest, the optimum disulfide volatility which produces wave compositions with the least odor can be determined. In addition, the sensitivity of olfactory receptors to certain disulfides should also be considered when selecting disulfides for use according to this invention. For example, di-n-heptyldisulfide formulated waving compositions had increased malodor compared to non-disulfide containing formulations due to the malodor of di-n-heptyldisulfide itself. See Example 2 and Table 3.

All publications, patent and articles referred to herein are expressly incorporated herein in toto by reference thereto. The following examples are presented to illustrate the present invention but are in no way to be construed as a limitation on the scope of the invention. It will be recognized by those skilled in the art that numerous changes and substitutions may be made without departing form the spirit and purview of the invention.

EXAMPLE 1

Synthetic Methods

Preparation of Di-i Octvldithiodiglycolate i-Octylthioglycolate (10.25 g, 0.05 mol; supplied by Bruno Bock) was heated in dimethyl sulfoxide (25 mL) at 80° C. for 18 hours under a nitrogen atmosphere. The mixture was poured into 500 mL of ice-water and stirred. Extraction with ethyl acetate (3×200 mL) and evaporation of (10.22 g, .0533 mol) in anhydrous methylene chloride. Decyl alcohol (8.44 g, 0.0533 mol) is added and the mixture is stirred at ambient temperature overnight. The mixture is washed with 10% aq. HCl, sat. NaHCO$_3$ solution and sat. NaCl. The organic layer is dried over MgSO$_4$, filtered and the solvent evaporated to provide the title ester.

Di-n-butyldithiodiglycolate was obtained from Sigma-Aldrich. Di-n-heptyldisulfide was purchased from Lancaster.

EXAMPLE 2

Wave Formulations

Incorporation of a Disulfide in an Acid Wave Base (activator balancing solution)

Di-i-octyldithiodiglycolate was formulated into an acid wave base as follows. C12–C15 Pareth 12 (10 g) was melted until clear then removed from the heat. Di-i-octyldithiodiglycolate (0.05 g) was added and stirred until uniformly dispersed. One percent of this solution was added to a wave lotion base consisting of 3.75% ammonium hydroxide, 1% ammonium chloride, 0.02% disodium EDTA and 95% water. Immediately before use, 78 g of the disulfide containing acid wave base was mixed with 25 g of glyceryl monothioglycolate Incorporation of a Disulfide in an Activator The disulfide or thiol additive was added in the concentration indicated in Tables 3 and 4, to 200 g of neat glyceryl monothioglycolate (GMr) in a 250 mL beaker. This composition can be used as the activator in acid waves and packaged in its own tube.

EXAMPLE 3

Odor Evaluations

Odor evaluation was conducted by 3–4 panelists who rated the odors on a scale of 1–5 where 1=no malodor and 5=extreme malodor. The beaker containing the disulfide containing activator prepared according to Example 2 was covered with foil and allowed to sit for at least 5 minutes prior to odor evaluation. The results are shown in Tables 3 and 4. The disulfide or thiol containing activator (25.5 g, prepared according to Example 2) was added to 76 niL of perfume-free wave composition in a 250 mL beaker. The wave composition consisted of 3.75% ammonium hydroxide, 1.5% ammonium chloride, 0.2% disodium EDTA, and distilled water to 100%. To this solution was added two tresses of dark brown, virgin hair (1 inch wide, 6 inches long), that had been washed with a 10% solution of SLS and soaked in synthetic sweat[8] at 37° C. for 17 hr, then lightly rinsed. The beaker containing the GMT activator was covered with foil and was allowed to sit for 5 to 10 minutes prior to odor evaluation. The tresses were then allowed to process in the wave composition for 20 minutes at room temperature in a covered beaker. The tresses were rinsed with tap water, towel blotted, then added to 80 mL of Matrix Opticurl Rebonding Neutralizer and processed for 5 minutes. After rinsing, the damp hair was evaluated for odor. The results are shown in Table 3.

The odor reduction results with 0.1% i-octylthioglycolate as the odor reducing agent (obtained from Bruno Bock), shows that this material reduces odor in all three categories. Replacement of this thiol with 1/10 the level of its disulfide gives comparable odor results. The odor that was detected with 0.01% di-i-octyldithiodiglycolate is a petroleum-like sulfur smell of the disulfide itself. Reduction of the disulfide concentration to 0.005% removed the sulfur odor from GMT without adding the petroleum odor of the disulfide. At this level, the final odor results using the disulfide were better than those were from the i-octylthioglycolate. In duplicate experiments, all panelists preferred the GMT containing 0.005% disulfide compared to GMT alone for both formulation odor and post-perm hair odor. Thus, it is preferable to have less i-octylthioglycolate than di-i-octyldithiodiglycolate in the formulations of this invention.

The results indicate that the disulfide, di-i-octyldithiodiglycolate, reduces the thiol odor associated with a GMT wave in all three categories evaluated. Surprisingly, this material reduced odor best when used at the lowest concentration of about 0.005 to about 0.01 weight percent It may be that at higher concentrations, while odorous hydrogen sulfide odor may be removed, the odor detected is that of the disulfide, which is itself disagreeable. When used at about 0.005 weight percent level, panelists reported the waving composition and the hair smell more neutral, and less chemical than the other solutions. The post-perm hair odor rating of 1.1 means that there is essentially no odor left on the hair.

Di-butyldithiodiglycolate effectively lowers odor in the activator and in the waving composition. This material similarly works best at about 0.005 to about 0.01 weight percent of GMT. This result indicates the generality of the theory that a disulfide can lower the odor of sulfur based reducing agent. The dibutyldisulfide does however, leave a sulfur malodor on the hair that is more disagreeable than the original GMT odor. The diheptyldisulfide produces an odor itself that is more disagreeable than the GMT odor alone.

TABLE 3

Improvement of GMT malodor by addition of low levels of disulfides or thiols. Numbers are the average ratings of 3–4 panelists on a scale of 1–5 where 1 = no malodor, and 5 = extreme malodor

| ADDITIVE | wt % in GMT | ACTI-VATOR (GMT + additive) | WAVING COMPO-SITION (with activator) | ODOR of Hair |
|---|---|---|---|---|
| None | — | 3.8 | 3.6 | 2.8 |
| i-octylthioglycolate[9] | 0.1 | 2.5 | 3.3 | 1.8 |
| di-i-octyldithiodiglycolate | 0.005 | 2.2 | 2.1 | 1.1 |
| di-i-octyldithiodiglycolate | 0.01 | 2.5 | 3.0 | 1.8 |
| di-i-octyldithiodiglycolate | 0.1 | 2.5 | 2.3 | 2.8 |
| dibutyldithiodiglycolate | 0.005 | 2.0 | 2.0 | 3.5 |
| dibutyldithiodiglycolate | 0.01 | 2.8 | 3.8 | 4 |
| di-n-heptyldisulfide | 0.005 | 5 | 5 | — |
| di-n-heptyldisulfide | 0.01 | 5 | 5 | — |
| pantethine | 0.1 | — | 4.5 | 1.4 |
| pantethine | 1.0 | — | 3.0 | 2.8 |

TABLE 4

Improvement of GMT malodor by addition of low levels of disulfides or thiols. Numbers are the average ratings of 3–4 panelists on a scale of 1–5 where 1 = no malodor, and 5 = extreme malodor

| ADDITIVE | wt % in GMT | ACTI-VATOR (GMT + additive) | WAVING COMPO-SITION (with activator) | ODOR of Hair |
|---|---|---|---|---|
| None | — | 4.7 | 3.7 | 4.0 |
| glutathione disulfide | 0.1 | 3.7 | 4.0 | 3.7 |
| glutathione disulfide | 1.0 | 4.5 | 3.7 | 3.0 |

EXAMPLE 4

Half-Head Testing in the Salon

Hair was divided into two sections down the middle of the head and wrapped onto perm rods in the usual manner. Immediately prior to use, activator tube A (25.5 g), consisting of 80% glyceryl monothioglycolate, was added to 76 mL of wave composition C; this formulation is the control. Activator tube B (25.5 g), consisting of 80% glyceryl monothioglycolate and 0.005% di-i-octyldithiodiglycolate, was added to a second 76 mL portion of wave composition C; this formulation is the test. The composition of wave composition C is shown in Table 5. The control formulation was applied to one side of the head, while the test formulation was applied to the other side of the head simultaneously by two stylists. On two of the clients, odor was judged on each side of the head during processing. A plastic cap was placed over the curlers and processing was 20 minutes for normal hair; less for fine hair or color treated hair. The hair was rinsed for 5 minutes in a sink, towel blotted, and treated with a full bottle of Matrix Opticurl Rebonding Neutralizer for 5 minutes. Hair was rinsed for 5 minutes and curlers were removed. Each side of the head was smelled by 3–4 judges to access post-perm odor.

TABLE 5

Wave Composition C

| | |
|---|---|
| water | 88% |
| tetrasodium EDTA | 0.1% |
| polyquaternium-22 | 0.4% |
| ammonium thioglycolate | 5.3% |
| ammonium hydroxide | 4.6% |
| fragrance | 0.6% |
| $C_{12-15}$ ethoxylated fatty alcohol | 0.9% |

During processing, the side of the head treated with the test solution containing disulfide (activator tube B) had noticeably lower odor. Post-perm odor was also lower on the side of the head treated with the test solution containing disulfide for 4 of the 5 clients. Hair treated with the test solution had a more neutral scent than the side treated with the regular GMT wave composition and the curl, combing and feel were identical on both sides.

REFERENCES

1. U.S. Pat. No. 4,547,365 (1985).
2. U.S. Pat. No. 4,560,554 (1985).
3. U.S. Pat. No. 5,554,364 (1996).
4. E. T. Borish in "Hair and Hair Care", D. H. Johnson ed. Marcel Dekker: New York 1997, p.174.
5. Nandagiri, A.; Solka, B.; Kocis, J. U.S. Pat. No. 5,553,363 (1996).
6. Neill, P.; Brandt, L. U.S. Pat. No. 5,554,364 (1996).
7. log P=log (concentration of substrate in octanol/concentration of substrate in water) wherein P=the partition coefficient of a substrate between octanol and water.
8. Recipe for synthetic sweat: 10 g sodium chloride, 1 g potassium hydrogen phosphate, 0.25 g histidine, lactic acid to adjust pH to 3.2 and water to make 1 L.
9. The i-octylthioglycolate sample contained approximately 5% di-i-octyldithioglycolate as determined by NMR analysis.

We claim:

1. A hair treatment composition effective in reducing malodor resulting from contacting hair with a sulfur-based reducing agent, wherein the composition comprises a water-insoluble disulfide having a log P value greater than about 1.

2. The composition according to claim 1, wherein the water-insoluble disulfide is incorporated into a composition selected from the group consisting of a pretreatment composition, a neutralizer composition, a sulfur-based reducing agent composition, an activator balancing solution, a post-treatment composition, and mixtures thereof.

3. The composition according to claim 2, wherein the water-insoluble disulfide is incorporated into a composition comprising the sulfur-based reducing agent, the activator balancing solution, or both.

4. The composition according to claim 3, wherein the water-insoluble disulfide is selected from the group consisting of: dithiodigeraniol, n-dodecyl-1,2-dithiolane-3-pentanoate, di-n-octyldithiodiglycolate, di-i-octyldithiodiglycolate, n-decyl-1,2-dithiolane-3-pentanoate, n-octyl-1,2-dithiolane-3-pentanoate, i-octyl-1,2-dithiolane-3-pentanoate, n-butyl-1,2-dithiolane-3-pentanoate, di-n-butyldithiodiglycolate, 5-phenyl-1,2-dithio-3-one, dithiodicitronollol, dithiodilinalol, dithiodi017,8perpineol, 3-[1,2-(hydroxyethyl)butyldisulfanyl]-hexan-1-ol, 6,8-dithiooctanoic acid, 6,8-dithiooctanoic acid methyl ester, dithiodiglycolamide siloxanes, silicone disulfides and mixtures thereof.

5. The composition according to claim 4, wherein the water-insoluble disulfide is di-i-octyldithiodiglycolate.

6. The composition according to claim 5, wherein the composition contains i-octylthioglycolate and di-i-octyldithiodiglycolate, the latter present in greater amounts.

7. A hair treatment composition for use in an acid wave product containing a sulfur-based reducing agent, wherein the composition is effective in reducing malodor resulting from contacting hair with the sulfur-based reducing agent, the composition comprising a disulfide in an amount of less than about 0.005%.

8. The composition according to claim 7, wherein the amount of disulfide is about 0.01% or less relative to the amount of reducing agent contained in the acid wave product.

9. The composition according to claim 8, wherein the reducing agent is glyceryl monothioglycolate.

10. The composition according to claim 9, wherein the disulfide is selected from the group consisting of di-i-octyldithiodiglycolate, pantethine, dithiodiglycolainide siloxanes and silicone disulfides.

11. The composition according to claim 10, wherein the amount of disulfide is about 0.005% or less relative to the amount of glyceryl monothioglycolate.

12. A hair treatment composition effective in reducing malodor resulting from contacting hair with a sulfur-based reducing agent, wherein the composition comprises a disulfide in an amount of about 0.1% or less, and wherein the disulfide is not pantethine.

13. The composition according to claim 12, wherein the disulfide is incorporated into a composition selected from the group consisting of a pretreatment composition, a neutralizer composition, a sulfur-based reducing agent composition, an activator balancing solution, a post-treatment composition, and mixtures thereof.

14. The composition according to claim 12, wherein the disulfide is selected from the group consisting of di-i-octyldithiodiglycolate, dithiodiglycolamide siloxanes and silicone disulfides.

15. A kit for permanently waving hair comprising (a) a waving composition containing a sulfur-based reducing agent in an amount effective to cleave disulfide bonds in the hair, (b) a neutralizing composition, and (c) a water-insoluble disulfide having a log P value greater than about 1.

16. The kit of claim 15, wherein the disulfide is present in the neutralizer composition.

17. The kit of claim 16 wherein the neutralizer composition contains from about 0.002 to about 0.01% disulfide by weight.

18. The kit of claim 16 wherein the disulfide is present in a pretreatment composition in an amount of from about 0.05 to about 2% by weight.

19. The kit of claim 16 wherein the disulfide is present in a post-treatment composition.

20. The kit of claim 15 wherein the disulfide is present in the waving composition.

21. The kit of claim 20 wherein the waving composition comprises an activator composition containing glyceryl monothioglycolate as the reducing agent and a balancing solution, the activator composition and the balancing solution being mixed prior to application to the hair, and the disulfide being present in the activator composition.

22. The kit of claim 20 wherein the waving composition comprises an activator composition containing glyceryl monothioglycolate as the reducing agent and a balancing solution, the activator composition and the balancing solution being mixed prior to application to the hair and the disulfide being present in the balancing solution composition.

23. The kit of claim 15, 16, 20, 21, or 22 wherein the disulfide is between about 0.00005 to about 5% by weight based on the amount of reducing agent contained in the waving composition.

24. The kit of claim 23 wherein the water-insoluble disulfide is selected from the group consisting of: dithiodigeraniol, n-dodecyl-1,2-dithiolane-3-pentanoate, di-n-octyldithiodiglycolate, di-i-octyldithiodiglycolate, n-decyl-1,2-dithiolane-3-pentanoate, n-octyl-1,2-dithiolane-3-pentanoate, i-octyl-1,2-dithiolane-3-pentanoate, n-butyl-1,2-dithiolane-3-pentanoate, di-n-butyldithiodiglycolate, 5-phenyl-1,2-dithio-3-one, dithiodicitronellol, dithiodilinalol, dithioditerpineol, 3-[1,2-(hydroxyethyl) butyldisulfanyl]-hexan-1-ol, 6,8-dithiooctanoic acid, 6,8-dithiooctanoic acid methyl ester, dithiodiglycolamide siloxanes, silicone disulfides and mixtures thereof.

25. The composition according to claim 24, wherein the disulfide is di-i-octyldithiodiglycolate.

26. A method of permanently waving hair, wherein said method has reduced malodor, comprising:
   (a) first contacting the hair with a waving composition containing a sulfur-based reducing agent in an amount effective to cleave disulfide bonds in the hair;
   (b) subsequently contacting the hair with a neutralizing composition containing an oxidizing agent to re-form the disulfide bonds in the hair; and
   (c) before, during or after either step (a) or step (b), contacting the hair with a water-insoluble disulfide having a log P value of greater than about 1.

27. A kit for permanently waving hair with an acid wave comprising (a) an activator composition containing glyceryl monothioglycolate in an amount effective to cleave disulfide bonds in hair, (b) a neutralizing composition, and (c) a disulfide present in a composition contained in the kit in an amount of less than 0.005% by weight.

28. A method of permanently waving hair with an acid wave, wherein said method has reduced malodor, comprising:
   (a) first contacting the hair with an activator composition comprising glyceryl monothioglycolate in an amount effective to cleave disulfide bonds in the hair;
   (b) subsequently contacting the hair with a neutralizing composition comprising an oxidizing agent to re-form the disulfide bonds; and
   (c) before, during or after either step (a) or step (b), contacting the hair with a disulfide, the disulfide being present in the activator composition, in the neutralizer composition, or in a hair treatment composition, in an amount of less than 0.005% by weight.

29. A permanent hair waving kit comprising (a) a waving composition containing a sulfur-based reducing agent in an amount effective to cleave disulfide bonds in the hair; (b) a neutralizing composition containing an oxidizing agent, and (c) a disulfide, the disulfide present in a composition contained in the kit in an amount of less than 0.1% by weight, wherein the disulfide is not pantethine.

30. A method of permanently waving hair, wherein said method has reduced malodor, comprising:
   (a) first contacting the hair with a waving composition containing an amount of a sulfur-based reducing agent effective to cleave disulfide bonds in the hair;
   (b) subsequently contacting the hair with a neutralizing composition containing an oxidizing agent to re-form the disulfide bonds; and
   (c) before, during or after either of step (a) or step (b), contacting the hair a disulfide, the disulfide being present in the waving composition, the neutralizer composition, or a hair treatment composition in an amount of about 0.1% or less, and wherein the disulfide is not pantethine.

31. A permanent hair waving kit comprising (a) a waving composition containing a sulfur-based reducing agent in an amount of from about 1 to about 18% by weight of the waving composition; (b) a neutralizing composition, and (c) a disulfide in an amount of from about 0.00005 to about 5 weight percent based on the amount of reducing agent, wherein the disulfide is not pantethine.

32. A method of reducing malodor resulting from contact of hair with a sulfur-based reducing agent comprising contacting the hair with a hair treatment composition comprising a disulfide in an amount of less than about 0.005% by weight of the composition.

33. A method of reducing malodor resulting from contacting hair with an amount of a sulfur-based reducing agent comprising contacting the hair with a hair treatment composition agent comprising a disulfide in an amount of about 0.1% or less, and wherein the disulfide is not pantethine, said composition being effective in reducing malodor resulting from contacting hair with the sulfur-based reducing agent.

34. The methods of claim 31, 32 or 33 wherein the disulfide has a log P value of greater than about 1.

* * * * *